(12) United States Patent (10) Patent No.: US 9,168,274 B1
Gropper (45) Date of Patent: Oct. 27, 2015

(54) METHOD TO REDUCE INTOXICATION FROM ETHANOL IN HUMANS

(71) Applicant: Jonathan Gropper, Marlton, NJ (US)

(72) Inventor: Jonathan Gropper, Marlton, NJ (US)

( * ) Notice: Subject to any disclaimer, the term of this patent is extended or adjusted under 35 U.S.C. 154(b) by 11 days.

(21) Appl. No.: 14/055,426

(22) Filed: Oct. 16, 2013

Related U.S. Application Data

(60) Provisional application No. 61/750,537, filed on Jan. 9, 2013.

(51) Int. Cl.
*A01N 63/00* (2006.01)
*A61K 35/74* (2015.01)
*A61K 45/06* (2006.01)

(52) U.S. Cl.
CPC ............... *A61K 35/74* (2013.01); *A61K 45/06* (2013.01)

(58) Field of Classification Search
None
See application file for complete search history.

(56) References Cited

U.S. PATENT DOCUMENTS

2003/0211172 A1* 11/2003 Jones et al. ................... 424/646

OTHER PUBLICATIONS

Adachi et al., Agric. Biol. Chem., 42(12):2331-2340 (1978).*

* cited by examiner

*Primary Examiner* — Blaine Lankford, Jr.
*Assistant Examiner* — Thomas J Visone
(74) *Attorney, Agent, or Firm* — Stanley H. Kremen

(57) ABSTRACT

The Present Invention aims to diminish the effects of alcohol consumption by breaking down the "stacked" excess alcohol in the digestive track through its probiotic element which effectively "eats" away at the alcohol before the liver has to process it. It comprises a personal dose of *Acetobacter aceti*, which is a benign microorganism that is ubiquitous in the environment, existing in alcoholic ecological niches such as flowers, fruits, honey bees, as well as in water and soil.

13 Claims, No Drawings

METHOD TO REDUCE INTOXICATION FROM ETHANOL IN HUMANS

CROSS REFERENCE TO RELATED APPLICATIONS

This Present Application is the nonprovisional counterpart of U.S. Provisional Patent Application Ser. No. 61/750,537 which was filed on Jan. 9, 2013, and is incorporated by reference herein in its entirety. The Present Application claims the benefit of and priority to said Provisional Patent Application Ser. No. 61/750,537.

BACKGROUND OF THE INVENTION

There is over 120 Billion dollars of alcohol products (Beer, Liquor & wine) is sold annually in the United States alone. According to the World Health Organization, the US is not even the largest drinking market. The world drank the equivalent of 6.1 liters of pure alcohol per person in 2005, according to a report from the World Health Organization. The biggest drinkers are mostly found in Europe and in the former Soviet states. Moldovans are the most bibulous, getting through 18.2 liters each, nearly 2 liters more than the Czechs in second place. Over 10 liters of a Moldovan's annual intake is reckoned to be 'unrecorded' home-brewed liquor, making it particularly harmful to health. Such moonshine accounts for almost 30% of the world's drinking. The WHO estimates that alcohol results in 2.5 m deaths a year, more than AIDS or tuberculosis. In Russia and its former satellite states one in five male deaths is caused by alcohol.

When Alcohol is consumed, be it Beer, Liquor or Wine it is predominantly broken down in one's liver. Blood Alcohol Level increases when the body absorbs alcohol faster than it can eliminate it. Seeing as the average healthy person can only eliminate about one dose of alcohol per hour, drinking several drinks per hour over a few hours will significantly increase one's Blood Alcohol Level. The liver breaks down Alcohol (Ethanol) through oxidation. An enzyme in the liver called alcohol dehydrogenase strips electrons from ethanol to form acetaldehyde. Another enzyme, called aldehyde dehydrogenase, converts the acetaldehyde, in the presence of oxygen, to acetic acid, a nutrient.

Appearing below is the chemical structure of acetic acid.

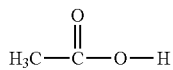

The COOH radical is typical of all organic acids. As can be seen, there is a double bond between the oxygen atom and the central carbon atom (C=O). When ethanol is oxidized to acetic acid, two protons and two electrons are also produced. The acetic acid can be used to form fatty acids or can be further broken down into carbon dioxide and water.

The liver can only process a set amount of alcohol per hour. The remainder gets "stacked" in the body, which is why people end up experiencing side effects for a prolonged period of time. As rule of thumb, an average person can eliminate 0.5 oz (15 ml) of alcohol per hour. So, it would take approximately one hour to eliminate the alcohol from a 12 oz (355 ml) can of beer. The average person consumes more than 3 drinks per hour in a given social event. This excess can lead to the over taxation of the liver, basic nervous and pulmonary functions as well as blood poisoning and death.

SUMMARY OF THE INVENTION

The Present Invention aims to diminish the effects of alcohol consumption by breaking down the "stacked" excess alcohol in the digestive track through its probiotic element which effectively "eats" away at the alcohol before the liver has to process it. This probiotic element is on the FDA's Generally Recognized as Safe (GRAS) list and as such has been shown to be adequately safe under the conditions of its intended. Not stopping there, the Present Invention actually generates acetic acid, which is a nutrient.

The Present Invention is comprised of a personal dose of *Acetobacter aceti*, which is a benign microorganism that is ubiquitous in the environment, existing in alcoholic ecological niches such as flowers, fruits, honey bees, as well as in water and soil. It has a long history of safe use in the fermentation industry for the production of acetic acid from alcohol. There are no reports in the literature suggesting that *Acetobacter aceti* is a pathogen in humans or animals. It also is not considered a plant pathogen.

DETAILED DESCRIPTION OF THE INVENTION

The process of the Present Invention consists of cultivating and growing the bacteria which is then turned into powder form after drying and inserted into set size capsules (e.g., 50 mg and 25 mg). taken orally.

*Acetobacter Aceti* as an organism takes ethanol and breaks it down into acetic acid with the presence of oxygen. By ingesting the pill, the bacteria are introduced to the ethanol from the alcoholic drinks in the stomach which is in turn broken down by the bacteria as the stomach is not devoid of oxygen. Since the bacteria resides optimally in a pH of 4-5 and the stomach pH is lower (more acidic), the bacteria's lifespan is limited not only by the ethanol content but also by the hostile environment. The bacteria will be present long enough to reduce the amount of alcohol that could be absorbed into one's body, and by doing so with proper dosage, can either reduce or eliminate the effects of alcohol in one's body as it prevents the liver from being overwhelmed and excess alcohol from entering the bloodstream and causing one to become intoxicated. It should be noted that *Acetobacter Aceti* is on the FDA's GRAS Generally Recognized as Safe list.

*Acetobacter aceti* is a gram-negative bacterium which is motile by peritrichous flagella. It is obligately aerobic possessing only the ability for respiratory metabolism with no fermentative ability. *Acetobacter aceti* does not form endospores. *Acetobacter aceti* produces acetic acid from ethanol in alcoholic niches in the environment. Acetate and lactate are oxidized to $CO_2$ and $H_2O$ by the organism. The optimum temperature for growth is between 25° to 30° C., and the optimum pH lies between 5.4 and 6.3.

There are no reports in the literature that *Acetobacter aceti* is capable of producing toxins active against humans or animals, nor are there reports of *A. aceti* causing infection in humans or animals. It does not produce enzymes or other extracellular factors normally associated with virulence. There is no reason to suspect that *A. aceti* could acquire or transfer any virulence factors. This bacterium does possess plasmids which are responsible for the production of enzymes used in acetic acid production. These plasmids have been shown to be transferred to other members of the species in the laboratory under optimal conditions. However, there is no evidence of plasmid transfer between strains of *Acetobacter aceti* or related species in the environment. Its unique ecological niches are such that it is unlikely that a second recipient or donor microorganism would be present in quantities sufficient for plasmid exchange to occur.

Biochemical characteristics of *Acetobacter aceti* virtually preclude it as being a threat to human health. Although it grows well with ethanol as a source of carbon, glucose has been shown to actually decrease the growth rate in culture, especially when other carbon sources were present. In addition, industrial strains may have been selected so that they do not have the ability to grow on glucose or so that they utilize very specific amino acids as nitrogen sources. This may result in growth inhibition in the presence of alternate amino acids.

In summary, *Acetobacter aceti* has no demonstrated virulence factors. It is not part of the normal flora of human skin or the body and is not expected to survive in a human host for sustained periods of time. The only threat to human health would lie in a massive contamination event in which workers may be exposed to extraordinarily high concentrations of the bacterium, and perhaps, develop an allergic or immunological reaction. It appears, however, because the bacterium is used for acetic acid production, should such a contamination event occur, the acetic acid would present a greater threat to workers than the bacterium itself. The potential for human virulence is virtually nonexistent for *Acetobacter aceti*.

Risks from use of the recipient microorganism *acetobacter aceti* are low. *acetobacter aceti* is a benign microorganism that is included in the FDA's GRAS list. It is not pathogenic to humans or animals. Although it often comes in contact with humans due to its widespread presence in the environment, it does not colonize human skin nor does it inhabit the human body. There are no reports in the literature suggesting any allergic or immunologic responses to the bacterium that has been used for decades in fermentation facilities.

In the Present Invention, the *Acetobacter aceti* vinegar culture may be isolated from sugar cane juice, rotten apples, flowers, wine, canal water and vinegar as a primary source for *Acetobacter* by continuous sub-culturing on standard medium glucose, yeast extract and calcium carbonate (GYC).

To prepare ~500 ml of liquid *Acetobacter* media, add the following:
  Glucose—10 g
  Peptone—2.5 g
  Yeast extract—2.5 g
  $Na_2HPO_4$—1.35 g
  Citric acid—0.75 g
  Distilled water—500 ml
Then:
1. Prepare media as outlined
2. Autoclave to sterilize media.
3. Streak/inoculate *Acetobacter* onto plates or in media.
4. Incubate cells at 26° C. for 2-3 days.
5. If using a freeze dried source of *Acetobacter* (ex. ATCC shipment), growth may take up to 4 days.

The *acetobacter aceti* is then ingested by persons as a pill, capsule, a liquid or gelatin solution, suspension, or mixture. This preparation will neutralize the effects of alcohol by turning ethanol into acetic acid.

TABLE 1

| Alcohol Elimination Rate | | | | |
|---|---|---|---|---|
| Alcohol elimination rate: | | | | |
| | .015 to .020 | grams per deciliter per hour | | |
| | 15 ml/hr for a normal liver | | | |
| 1 shot glass | 1.5 oz | 45 ml | actually about 0.5 oz of pure alcohol | 15 ml of alcohol |

TABLE 2

Standard Drink Chart

| Alcohol | Amount (ml) | Amount (fl oz) | Serving size | Alcohol (% by vol.) | Alcohol |
|---|---|---|---|---|---|
| 80 proof liquor | 44 | 1.5 | One shot | 40 | 0.6 US fl oz (18 ml) |
| Table wine | 148 | 5 | One glass | 12 | 0.6 US fl oz (18 ml) |
| Beer | 355 | 12 | One can | 5 | 0.6 US fl oz (18 ml) |

Table 1 (above) shows the rate of elimination of the effects of alcohol in humans. Table 2 (above) shows how much alcohol is contained in various alcoholic beverages.

The American Medical Association has defined the blood alcohol concentration level of impairment for all people to be 0.04 grams/100 milliliters of blood with 5 liters of blood in the average 70 kg person, 2 grams of alcohol creates impairment. With very high concentrations—greater than 0.35 grams/100 milliliters of blood (equivalent to 0.35 grams/210 liters of breath)—a person can become comatose and die. With 5 liters of blood in the average 70 kg person, 17.5 grams of alcohol create a likelihood of death.

To calculate how much *acetobacter aceti* would be needed to neutralize 15 ml of pure alcohol, we must consider that based on 50 g of bacteria, the maximum production rate of acetic acid by the bacterial films of *acetobacter aceti* M7 grown on the shell-side surface of the tubes was 38.0 g/lh, worst case about 2 g.

It is anticipated that the average formulation of a pill or capsule of the Present Invention would comprise approximately 50 mg of bacteria.

TABLE 3

| Normal Drinking 9 PM to 2 AM - 5 hours (number of drinks = 6): | | |
|---|---|---|
| ml of alcohol | 90 ml | |
| liver processing | 75 ml | (15 ml/hr) |
| Present Invention overage | 15 ml | (0.025 gm) |

A single pill (0.05 gm) converts 2 ml/hr (0.002 gm/hr). That amounts to 10 ml/night or 0.01 gm over 5 hours. A double dose would convert 4 ml/hr, which would amount to 20 ml/night or 0.02 gm over 5 hours.

TAble 4

| Binge Drinking 7 PM to 2 AM - 7 hours (number of drinks = 10) | | |
|---|---|---|
| ml of alcohol | 150 ml | |
| liver processing | 105 ml | (15 ml/hr) |
| Present Invention overage | 45 ml | (0.045 gm) |

Here, a single pill (0.05 gm) converts 14 ml/night (over 0.014 gm over a 7-hour period). A double dose converts 28 ml/night (0.028 gm over a 7-hour period).

As can be seen from Tables 3 and 4 above, the combination of normal processing of alcohol in the liver with the production of acetic acid from ingestion of *acetobacter aceti* is an effective means of sobering an individual who consumed an excessive amount of alcohol.

Not only can this method be effective by a person ingesting a capsule or pill, but it may also be effective by ingesting "shot" drinks. "Shot" drinks are in small containers, and the active ingredients may be dissolved in a liquid or gelatin medium.

The bacteria may also be the ingredient in a liquid suspension that is ingested by people wishing to overcome the effects of alcohol. In a liquid suspension, freeze-drying of the bacteria may not be required, because an environment is being created wherein the bacteria can be partially active. Furthermore, any formulation of any type may include stabilizers.

In addition to the active ingredients already disclosed, the formulation may also contain vitamins and other additional ingredients to increase metabolism. Possible vitamin ingredients comprise Vitamin B6, Vitamin B12, Niacin (Vitamin B3), or Folic Acid (Vitamin B9). The other additional ingredients (mentioned above) could include Citcoline, Tyrosine, Phenylalanine, Taurine, Malic Acid Glucuronolactone, or Caffeine. These latter ingredients are known stimulants.

I claim:

1. A method to reduce intoxication from ethanol in a person comprising:
   a) cultivating and growing *Acetobacter Aceti* bacteria;
   b) drying the *Acetobacter Aceti* bacteria;
   c) creating a powder from the dried *Acetobacter Aceti* bacteria;
   d) manufacturing one or more delivery agents each containing a desired amount of the powder; and
   e) providing at least one of said delivery agents to the person prior to said person imbibing alcohol, whereby at least a portion of the alcohol is converted into acetic acid by the *Acetobacter Aceti* bacteria in the person's stomach.

2. The method of claim 1 wherein the at least one of said delivery agents is a pill or capsule.

3. The method of claim 1 wherein the at least one of said delivery agents is a container of suitable size containing a liquid or a gel.

4. The method of claim 3 wherein the powder is dissolved in said liquid or gel.

5. The method of claim 3 wherein the powder is insoluble in said liquid or gel, but instead is mixed with said liquid or gel.

6. The method of claim 1 wherein the at least one of said delivery agents is a liquid suspension.

7. The method of claim 1 wherein the at least one of said delivery agents additionally comprises one or more stabilizers.

8. The method of claim 1 wherein one or more vitamins are added to the powder in said delivery agent.

9. The method of claim 8 wherein said one or more vitamins are selected from the group consisting of Vitamin B6, Vitamin B12, Niacin, and Folic Acid.

10. The method of claim 9 wherein more than one vitamin is selected from said group and wherein each vitamin is different from the other.

11. The method of claim 1 wherein one or more stimulants are added to the powder in said delivery vehicle.

12. The method of claim 11 wherein said one or more stimulants are selected from the group consisting of Citcoline, Tyrosine, Phenylalanine, Taurine, Malic Acid, Glucuronolactone, and Caffeine.

13. The method of claim 12 wherein more than one stimulant is selected from said group and wherein each stimulant is different from the other.

* * * * *